United States Patent [19]
Heiker et al.

[11] Patent Number: 4,590,179
[45] Date of Patent: * May 20, 1986

[54] MEDICAMENTS CONTAINING AMINO-CYCLITOL DERIVATIVES

[75] Inventors: Fred R. Heiker; Lutz Müller; Walter Puls; Hilmar Bischoff, all of Wuppertal, Fed. Rep. of Germany

[73] Assignee: Bayer Aktiengesellschaft, Leverkusen, Fed. Rep. of Germany

[*] Notice: The portion of the term of this patent subsequent to Jul. 2, 2002 has been disclaimed.

[21] Appl. No.: 692,100

[22] Filed: Jan. 16, 1985

Related U.S. Application Data

[62] Division of Ser. No. 369,761, Apr. 19, 1982, Pat. No. 4,526,784.

[30] Foreign Application Priority Data

May 5, 1981 [DE] Fed. Rep. of Germany ....... 3117705
Aug. 19, 1981 [DE] Fed. Rep. of Germany ....... 3132691

[51] Int. Cl.⁴ .............................................. A61K 31/73
[52] U.S. Cl. ..................................................... 514/25

[58] Field of Search ................. 536/18.6, 17.2, 18.5; 424/180; 514/25

[56] References Cited

U.S. PATENT DOCUMENTS 4,254,256 3/1981 Otani et al. ...................... 536/17.2

FOREIGN PATENT DOCUMENTS 21170 2/1979 Japan .................................... 536/4.1

Primary Examiner—Johnnie R. Brown
Assistant Examiner—Elli Peselev
Attorney, Agent, or Firm—Sprung, Horn, Kramer & Woods

[57] ABSTRACT

The invention relates to amino-cyclitol derivatives of Formula (I) and their individual anomers. Also included in the invention are processes for the manufacture of said amino-cyclitol derivatives and their individual anomers, compositions containing said amino-cyclitol derivatives or anomers; and methods for the use of said derivatives and anomers for the treatment of diabetes, adiposity or hyperlipaemia.

5 Claims, No Drawings

MEDICAMENTS CONTAINING AMINO-CYCLITOL DERIVATIVES

This is a division of application Ser. No. 369,761, filed 4/19/82, U.S. Pat. No. 4,526,784.

The present invention relates to certain aminocyclitol derivatives, to a process for their production and to their use as medicaments, particularly in the therapy of diabetes, adiposity and hyperlipaemia.

Compounds of the formula

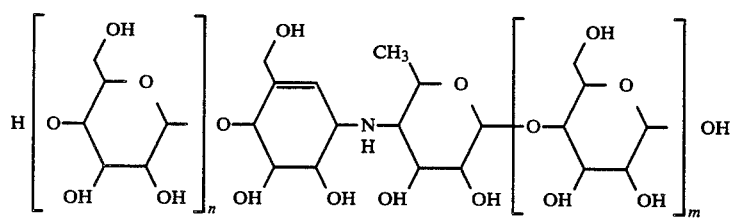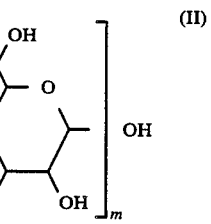

(II)

are known from DE-OS (German Published Specification) No. 2,726,207. They can be obtained by the reaction of the corresponding acetobromo compounds with the particular alcohols. However, where compounds of formula (II) with n+m=0 are required, this process is not yet optimum insofar as the synthesis in this special case is complicated and gives comparatively low yields.

According to the present invention where are provided compounds which are aminocyclitol derivatives of the formula

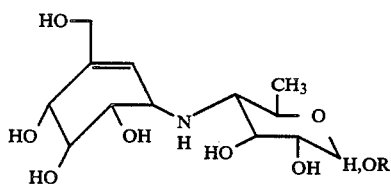

(I)

in which
R denotes an optionally substituted alkyl or alkenyl group, and in which the symbol "H,OR" indicates that both possible stereoisomeric formulae are included.

Preferably, the compounds of the present invention are in crystalline form, even as an anomeric mixture. In addition to the anomeric mixture, the invention also relates to the individual anomers, those of the α form being preferred.

In compounds according to the present invention radical R, when an alkyl group, preferably represents a straight-chain or branched alkyl group having 1 to 30, in particular 1 to 18, and very particularly preferably 1 to 6, carbon atoms. Methyl, ethyl, n-propyl, i-propyl, n-butyl, t-butyl, n-hexyl, n-octyl, oct-2-yl, dodecyl, lauryl, cetyl and stearyl may be mentioned as examples, and methyl, ethyl and i-propyl are particularly preferred.

The alkyl radicals of radical R can carry one or more, preferably 1 to 5, identical or different substituents. The following may be mentioned as examples of such substituents: hydroxyl, alkoxy having preferably 1 to 4 carbon atoms (in particular methoxy and ethoxy); amino, monoalkylamino and dialkylamino having preferably 1 to 4 carbon atoms per alkyl radical (in particular monomethylamino, monoethylamino, dimethylamino and diethylamino); mercapto, alkylthio having preferably 1 to 4 carbon atoms (in particular methylthio and ethylthio); halogen (preferably fluorine, chlorine and bromine); alkylcarbonyl having preferably 1 to 4 carbon atoms in the alkyl radical; carboxyl, nitro, cyano, the aldehyde function and the sulphonic acid group. A preferred substituted alkyl radical R is —CH$_2$—CH$_2$—Cl.

In compounds according to the present invention radical R, when an alkenyl group, preferably represents a straight-chain or branched alkenyl group having 2 to 6 carbon atoms and 1, 2 or 3 double bonds (for example allyl), which can carry 1 to 5, or preferably 1 or 2, substituents such as hydroxy, alkoxy having 1 to 4 carbon atoms, mercapto, alkylthio having 1 to 4 carbon atoms, halogen and nitro.

Preferred compounds according to the present invention are those in which R represents an alkyl group with 1 to 6 carbon atoms or an alkenyl group with 2 to 6 carbon atoms.

According to the present invention there is further provided a process for the production of a compound of the present invention, in which a substance of the general formula

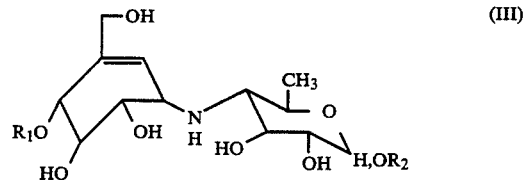

(III)

or an O-protected derivative thereof, in which
$R_1$ and $R_2$ represent identical or different monosaccharide or oligosaccharide radicals, radical $R_1$ being glycosidically bonded via oxygen to the remainder of the molecule and radical $R_2$ being bonded in any desired manner via oxygen to the remainder of the molecule, and the symbol "H, OR$_2$" indicating that both possible stereoisomeric compounds of formula (III) are included, is reacted with an alcohol ROH in the presence of a proton acid HX, wherein
R has the abovementioned meaning and
X represents the radical of a strong inorganic non-oxidising acid, and if the α-anomer is required, the α-anomer is isolated from the resulting anomer mixture.

The protective groups of the O-protected derivative are those protective groups which are customary in sugar chemistry, for example the acetyl group.

The process for cleaving oligosaccharides by just aqueous proton acids is known. However, if compounds of the formula (III) are employed in this reaction, the tricyclic oxazolidine of the formula

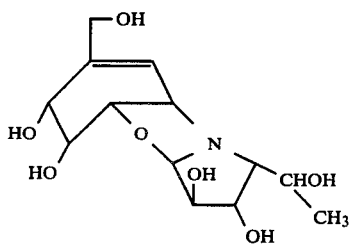

is obtained instead of a compound of formula (I) with R=H.

This result was to have been expected for any attempt to cleave oligosaccharides of formula (III) with acids, since extensive work by Paulsen and coworkers has shown that under acid conditions, in the case of carbohydrates having amino and alkylamino groups in the 4-position, a condensation of this nucleophilic grouping with the aldehyde function to form piperidine and pyrrolidine sugars occurs particularly readily. The intensive decomposition of the substances has been attributed to this ring formation and the subsequent side reactions (elimination, polymerisation and aromatisation). There are thus, in the literature, many examples in which only an extensive decomposition and partial separation of black polymeric substances are observed when attempts have been made to liberate 4-amino sugars by acid hydrolysis of their derivatives, for example glycosides.

In view of these results in the literature, it is so much the more surprising that, in the reaction according to the invention, the compounds of the formula (I) are obtainable in good yields as crystalline substances, initially as an anomer mixture.

In a particularly advantageous process according to the present invention, an alcohol ROH having 1 to 6 carbon atoms is employed and the starting compound is a compound of the formula (III) in which $R_1$ and $R_2$ are glucose or oligosaccharide radicals synthesised from glucose.

In general, the process according to the invention is carried out as follows:

A compound of the formula (I) (anomer mixture) is obtained by the reaction of a starting compound of formula (III) with an alcohol ROH in the presence of an inorganic proton acid HX, generally at a temperature of from 60° to 130° C., preferably from 60° to 100° C. normally during the course of at least 0.5 hour, in particular from 0.5 to 12 hours. A non-oxidising strong acid, for example sulphuric acid, phosphoric acid or preferably hydrochloric acid, is preferably employed as the inorganic proton acid HX.

In carrying out the process according to the invention, attention should be paid, in particular, to the following:

In general, the acid concentration should be from 0.5 to 4 normal. However, the concentration within this range is not arbitrary but is to be chosen in relation to the alcohol used. For this purpose, the optimum concentration to be chosen in each individual case must be determined, if necessary, by a few preliminary experiments. However, it is possible to state that in the case of methanol the acid concentration can vary in the upper range, without substantial decomposition occurring. However, if ethanol is used instead, the acid concentration should not exceed 1 to 2N.

Also with respect to the reaction temperature, the process optimum has to be determined as a function of the alcohol and the acid strength.

In general, conditions which are too mild lead only to a partial cleavage of the compounds of formula (III) employed, and under conditions which are too extreme predominant formation of the substance of formula (IV) or the stated decomposition reactions occur.

After the end of the reaction, the resulting reaction mixture may be neutralised with $Na_2CO_3$, filtered to separate off solid constituents and concentrated under reduced pressure. The residual viscous mass may then be taken up in water and chromatographed over an acid ion exchanger to separate off non-basic reaction products. The elution of the substances of the formula (I) (as anomer mixture) is generally carried out with a small quantity of 1% aqueous ammonia solution.

To separate off basic constituents which still remain, the basic eluate may be concentrated and chromatographed over aluminium oxide with methanol/water 3:1 (V/V). The substance-containing eluates are concentrated and the compounds which have been freed from the by-products may be recrystallised from methanol or a solvent mixture of methanol and isopropanol. The crystalline material obtained forms a conglomerate of crystals of the α and β glycosides of the compounds according to the present invention of formula (I). The pure anomers can then be obtained by fractional crystallisation and, if appropriate, selective protective group chemistry. In general, the β derivatives are less soluble than the α derivatives in methanol and can thus be obtained in pure form by recrystallisation. For the purification of the α derivatives, it is advisable to carry out the working-up with the introduction of protective groups.

The compounds according to the invention are inhibitors of glycoside hydrolases and are therefore suitable for the treatment of diseases in which an inhibition of these enzymes appears desirable, in particular the therapy of diabetes, adiposity and hyperlipaemia.

As stated above, the invention also relates to the use in medicine of the compounds of the invention.

The present invention provides pharmaceutical compositions containing as active ingredient a compound of the invention in admixture with an inert pharmaceutical carrier, e.g. a solid or liquefied gaseous diluent, or in admixture with a liquid diluent other than a solvent of a molecular weight-less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl-alcohol, glycerol monostearate; (h) adsorptive carriers, e.g. kaolin- and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present-invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diesease in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) or rectally. It can at times be necessary to deviate from those dosage rates which are normally found to be optimum, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the normal optimum minimum dosage rate, whilst other cases the normal optimum upper limit must be exceeded to achieve the desired results. Where larger amounts are administered it can be advisable to divide these into several individual administrations over the course of the day. The activity of the substances of the present invention of formula (I) were determined in vitro in the following saccharase inhibition test.

EXAMPLE A

Saccharase inhibition test in vitro

The saccharase inhibition test in vitro makes possible the determination of the enzyme-inhibiting activity of a substance by means of the comparison of the activity of the solubilised intestinal disaccharidase complex in the presence or in the absence (so-called 100% value) of the inhibitor. In this test, a virtually glucose-free saccharose (glucose <100 ppm) was used as the substrate, which determined the specificity of the inhibition test; the determination of the enzyme activity was based on the spectrophotometric determination of glucose liberated by means of glucose dehydrogenase and nicotinamide-adeninedinucleotide as the cofactor.

A saccharase inhibitor unit (SIU) is defined as that inhibiting activity which reduces a given saccharolytic activity by one unit (saccharase unit=SU) in a defined test batch; in this context, the saccharase unit is defined as that enzyme activity which, under given conditions, cleaves one μmol of saccarose per minute and thus leads to the liberation of one μmol each of glucose, which is determined in the test, and of fructose, which is not determined in the test.

The intestinal disaccharidase complex was obtained from porcine small intestinal mucosa, by tryptic digestion, precipitation from 66% ethanol at −20° C., taking up the precipitate in 100 mM phosphate buffer, pH 7.0, and subsequent dialysis against the same buffer.

100 μl of a dilution of the intestinal disaccharidase complex in 0.1M maleate buffer, pH 6.25, were added to 10 μl of a sample solution which was prepared such that the extinction of the test batch was at least 10%, but not more than 25%, below that of the 100% value, and the mixture was pre-incubated at 37° C. for 10 minutes. The dilution of the disaccharidase complex was adjusted to an activity of 0.1 SU/ml.

The saccharolytic reaction was then started by the addition of 100 μl of a 0.4M solution of saccharose (sucrose) ("SERVA 35579") in 0.1M of maleate buffer, pH 6.25, and was stopped, after an incubation time of 20 times at 37° C., by the addition of 1 ml of glucose dehydrogenase reagent (1 phial of glucose dehydrogenase mutarotase mixture lyophilised ("MERCK 14053") and 331.7 mg of β-nicotinamideadenine-dinucleotide (free acid, "BOEHRINGER" degree of purity I) dissolved in 250 ml of 0.5M tris buffer, pH 7.6). The glucose was determined by incubating the mixture at 37° C. for 30 minutes and finally carrying out a photometric analysis at 340 nm against a reagent blank (with the enzyme, but without the saccharose).

The calculation of the inhibiting activity of the incubitors is made difficult by the fact that even trivial changes in the test system, for example a 100% value which varies slightly from determination to determination, have, on the test result, an effect which can no longer be neglected. These difficulties are overcome by using a standard in parallel with each determination; the standard used was a saccharase inhibitor of the formula C$_{25}$H$_{43}$O$_{18}$N (acarbose), which had a specific inhibiting activity of 77,700 SIU/g and, when employed in quantities of from 10 to 20 ng in the test, led to an inhibition of the order of magnitude specified above. With a knowledge of the difference in the extinctions, at 340 nm, of the 100% value and the batch inhibited by the standard, it was possible, from the difference in extinction of the 100% value and the batch inhibited by the sample solution, and taking into account the quantity of inhibitor employed, to calculate in a known manner the specific inhibiting activity of the inhibitor, this activity being expressed in saccharase inhibitor units per gram (SIU/g).

Saccharase-inhibiting activity, in vitro, of compounds of the formula I are indicated in the following Table 1.

TABLE 1

Comparison: Substance of the formula (II) with n = 0 and m = 2 (Acarbose)

| | | SIU/g |
|---|---|---|
| | | 77,700 |
| Ia | (R:CH$_3$; according to Example 1) | 79,640 |
| Ib | (R:CH$_2$CH$_3$; according to Example 2) | 108,310 |
| Ic | (R:CH$_2$CH$_2$Cl; according to Example 3) | 30,300 |
| Id | (R:CH$_2$—CH=CH$_2$; according to Example 4) | 93,000 |
| Iα | (R:CH$_3$; according to Example 1b) | 365,200 |
| Iβ | | ~3,000 |

The examples which follow illustrate the production of compounds according to the present invention. In the examples, all percentage data are percentages by weight.

EXAMPLE 1

(a) Substance Ia 100 g of acarbose (a substance of the formula (II) with n=0 and m=2) were dissolved in 1,000 ml of absolute methanol which contained 10% of hydrogen chloride, and the solution was stirred at a temperature of 60° C. for 4 hours. The solution was thereafter neutralised with solid sodium carbonate and the precipitate formed was filtered off. The filtrate obtained was concentrated, under reduced pressure, to give a brown viscous syrup. This was dissolved in 500 ml of water and was introduced over a column containing 1,000 ml of ion exchanger resin ("Amberlite" IR (Trade Mark) 120H⊕). The column was then rinsed with water until non-basic constituents (glucose etc.) were no longer eluted. The substance Ia was then eluted from this column, using 1% strength aqueous ammonia solution. The basic eluate was concentrated to a syrup, taken up in 300 ml of a mixture of methanol and water (3:1, V/V) and chromatographed over a column containing 1,000 g of aluminium oxide (Woelm Neutral) (mobile phase: methanol/water 3:1; V/V). The substance-containing fractions were concentrated and the product Ia was crystallised from methanol/isopropanol (~4:1 V/V).

Yield: 21 g of Ia.

NMR spectroscopic characterisation of compound Ia (anomer mixture).

After acetylation, compound Ia was investigated by NMR spectroscopy. In this investigation, it was possible to establish the following chemical shifts (in ppm) for the protons of the aglycone R and of the amino sugar part:

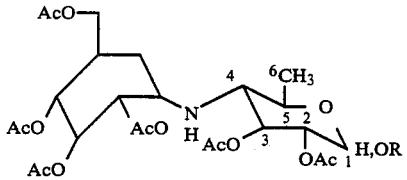

| Substance | Signal | α-OR | β-OR |
|---|---|---|---|
| I ac | 1-H | 4.80 | 4.31 |
| | 3-H | 5.26 | |
| | 4-H | 2.44 | 2.49 |
| R: CH$_3$ | 5-H | 3.61 | 3.27 |
| | 6-CH$_3$ | 1.25 | 1.31 |
| | R (CH$_3$) | 3.48 | 3.37 |

The measurements were effected in CDCl$_3$ at a frequency of 250 MHz.

(b) Preparation of the pure α- and β-anomers of the methylglycoside Ia

By fractional crystallisation from methanol, the β-anomer was separated off from a mixture of the methylglycosides (see Example 1a) to such an extent that the mother liquor contained about 80% of the α-methylglycoside. The syrup (17 g) remaining after concentration of the mother liquor was dissolved in 200 ml of absolute dimethylformamide and 6 ml of 48% strength HBr solution was added, whilst cooling with ice. Thereafter, isopropenyl methyl ether was added dropwise (approx. 100 ml over a period of 2 hours) at room temperature, until the substance with an Rf value of 0.5 (thin layer chromatography: silica gel sheets, Merck, mobile phase toluene/ethanol 3:1) was the principal product.

To work up the mixture, it was neutralised with solid sodium carbonate, filtered and concentrated. The residue was taken up in 200 ml of chloroform, and the organic phase was washed twice with 100 ml of water, dried over sodium sulphate and concentrated. Yield of crude product 21 g.

13 g of the di-isopropylidene compounds V were obtained by preparative column chromatography over silica gel 60 (Merck), using toluene/ethyl acetate 2:1 (V/V) as the mobile phase. An analytical sample was acylated to VI since V did not crystallise.

The free α-methylglycoside was prepared by dissolving the compound V in 60% strength aqueous acetic acid and stirring the solution at 60° C. for 4 hours. The substance I-α crystallised from methanol.

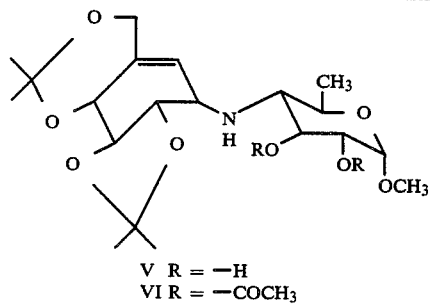

V R = —H
VI R = —COCH$_3$

Physical data:

| I-α | M.p. 157° C. | $[\alpha]_D^{20}$ = | +185.1° |
| | | (c = 0.8 H$_2$O) | |
| I-β | M.p. 208° C. | $[\alpha]_D^{20}$ = | +19.8° |
| | | (c = 0.5 H$_2$O) | |
| VI | M.p. 160° C. | $[\alpha]_D^{20}$ = | +146.5° |
| | | (c = 0.8 CHCl$_3$) | |

EXAMPLE 2

Substance Ib 10 g of acarbose were dissolved in 400 ml of absolute ethanol which contained 2.5% of hydrogen chloride, and the solution was stirred at 80° C. for 8 hours. The working-up was effected analogously to Example 1a and the product was recrystallised from methanol.

Yield: 0.7 g of Ib.

EXAMPLE 3

Substance Ic 100 g of acarbose were dissolved in 1,000 ml of absolute chloroethanol which contained 1.5% of hydrogen chloride, and the solution was stirred at 60° C. for 12 hours. The working-up was effected as in Example 1a and the product was recrystallised from methanol.

Yield: 90 g of Ic.

EXAMPLE 4

Substance Id 10 g of acarbose were dissolved in 400 ml of absolute allyl alcohol which contained 2% of hydrogen chloride and the solution was stirred at 90° C. for 7 hours. The working-up was effected analogously to Example 1a and the product was recrystallised from methanol.

Yield: 1.1 g of Id.

NMR spectroscopic characterisation of the compounds Ib-d.

After acetylation, the glycosides of the general formula (I) were investigated by NMR spectroscopy. In this investigation, it was possible to establish the following chemical shifts (in ppm) for the protons of the aglycone R and of the amino sugar part:

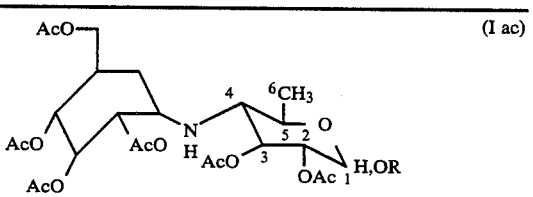

(I ac)

| Substance | Signal | α-OR | β-OR |
|---|---|---|---|
| Ib ac | 1-H | 4.92 | 4.39 |
| | 2-H | 4.79 | |
| | 3-H | 5.23 | |
| R: CH$_2$—CH$_3$ | 4-H | 2.42 | 2.49 |
| | 5-H | | 3.25 |
| R: —CH$_2$— | | 3.95–3.41 | |
| CH$_3$ | | 1.20 | |
| Ic ac | 1-H | 5.01 | 4.46 |
| | 2-H | 4.78 | |
| | 3-H | 5.28 | |
| R: CH$_2$—CH$_2$—Cl | 4-H | 2.44 | 2.49 |
| | 5-H | | 3.28 |
| | 6-CH$_3$ | 1.24 | 1.30 |
| R: —CH$_2$—C$_2$—Cl | | 4.24–3.60 | |
| Id ac | 1-H | 4.96 | 4.45 |
| | 2-H | 4.82 | |
| | 3-H | 5.30 | |
| R: CH$_2$—CH=CH$_2$ | 4-H | 2.43 | 2.50 |
| | 5-H | 3.65 | 3.26 |
| | 6-CH$_3$ | 1.24 | 1.30 |
| R: —CH$_2$— | | 4.37–3.92 | |
| —CH= | | 5.94–5.76 | |
| =CH$_2$ | | 5.35–5.15 | |

The measurements were effected in CDCl$_3$ at a frequency of 250 MHz.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A pharmaceutical composition containing as an active ingredient an aminocyclitol derivative in crystalline form of the formula

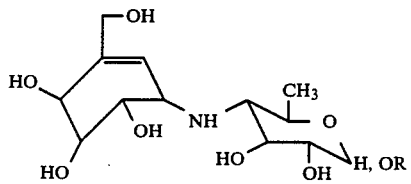

in which

R denotes $C_1$–$C_{30}$-alkyl which is unsubstituted or substituted by 1 to 5 substituents selected from hydroxyl, $C_1$–$C_4$-alkoxy, amino, mono- or di-alkylamino having 1 to 4 carbon atoms per alkyl radical, mercapto, $C_1$–$C_4$-alkylthio, halogen, $C_1$–$C_4$-alkylcarbonyl, carboxyl, nitro, cyano, the aldehyde function and a sulphonic acid group or a $C_2$–$C_6$-alkenyl group having 1 to 3 double bonds and optionally carrying 1 to 5 substituents selected from hydroxy, $C_1$–$C_4$-alkoxy, mercapto, $C_1$–$C_4$-alkylthio, halogen and nitro, and in which the symbol "H, OR" indicates that both possible stereoisomeric formulae are included in amount effective for treating adiposity, in admixture with an inert pharmaceutical carrier.

2. A pharmaceutical composition of claim 1 in the form of a sterile or physiologically isotonic aqueous solution.

3. A pharmaceutical composition in dosage unit form containing as an active ingredient an aminocyclitol derivative in crystalline form of the formula

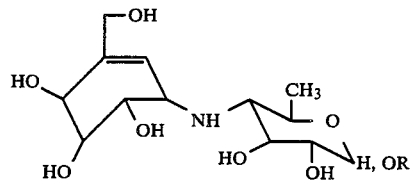

in which

R denotes $C_1$–$C_{30}$-alkyl which is unsubstituted or substituted by 1 to 5 substituents selected from hydroxyl, $C_1$–$C_4$-alkoxy, amino, mono- or di-alkylamino having 1 to 4 carbon atoms per alkyl radical, mercapto, $C_1$–$C_4$-alkylthio, halogen, $C_1$–$C_4$-alkylcarbonyl, carboxyl, nitro, cyano, the aldehyde function and a sulphonic acid group or a $C_2$–$C_6$-alkenyl group having 1 to 3 double bonds and optionally carrying 1 to 5 substituents selected from hydroxy, $C_2$–$C_4$-alkoxy, mercapto, $C_1$–$C_4$-alkylthio, halogen and nitro, and in which the symbol "H, OR" indicates that both possible stereoisomeric formulae are included in amount effective for treating adiposity, in admixture with an inert pharmaceutical carrier.

4. A pharmaceutical composition of claim 3 in the form of tablets, pills, dragees, capsules, ampoules, or suppositories.

5. A method of treating adiposity, in warm-blooded animals which comprises administering to the animals an active compound according to claim 1 in an amount effective for treating adiposity either alone or in admixture with a diluent or in the form of a pharmaceutical composition.

* * * * *